United States Patent [19]

Outtrup et al.

[11] Patent Number: 5,650,315
[45] Date of Patent: Jul. 22, 1997

[54] ALKALINE PROTEASES OBTAINABLE FROM BACILLUS SP. JA16-38A

[75] Inventors: Helle Outtrup, Ballerup; Claus Dambmann, Soeborg; Dorrit A. Aaslyng, Roskilde, all of Denmark

[73] Assignee: Novo Nordisk A/S, Bagsvaerd, Denmark

[21] Appl. No.: 107,687

[22] PCT Filed: Apr. 3, 1992

[86] PCT No.: PCT/DK92/00103

§ 371 Date: Aug. 18, 1993

§ 102(e) Date: Aug. 18, 1993

[87] PCT Pub. No.: WO92/17576

PCT Pub. Date: Oct. 15, 1992

[30] Foreign Application Priority Data

Apr. 3, 1991 [DK] Denmark ................... 0583/91

[51] Int. Cl.$^6$ ................. C12N 9/56; C12N 9/54; C12N 1/20; C11D 7/42
[52] U.S. Cl. ................. 435/222; 435/221; 435/252.5; 435/832; 510/392; 510/530
[58] Field of Search ................. 435/220, 221, 435/222, 252.5, 832–839; 252/174.12

[56] References Cited

U.S. PATENT DOCUMENTS

| | | | |
|---|---|---|---|
| 3,674,643 | 7/1972 | Aunstrup et al. | 435/221 |
| 3,723,250 | 3/1973 | Aunstrup et al. | 435/221 |
| 3,827,938 | 8/1974 | Aunstrup et al. | 435/221 |
| 3,905,869 | 9/1975 | Hidaka et al. | 435/221 |
| 4,002,572 | 1/1977 | te Nijenhuis | 252/99 |
| 4,052,262 | 10/1977 | Horikoshi et al. | 435/221 |
| 4,480,037 | 10/1984 | Ichishima et al. | 435/221 |
| 4,764,470 | 8/1988 | Durham et al. | 435/221 |
| 4,771,003 | 9/1988 | Stellwag et al. | 435/221 |
| 5,352,603 | 10/1994 | Vetter et al. | 435/221 |
| 5,429,765 | 7/1995 | Flower | 252/174.12 |

FOREIGN PATENT DOCUMENTS

| | | |
|---|---|---|
| 0204342 | 12/1986 | European Pat. Off. . |
| 0328229 | 8/1989 | European Pat. Off. . |
| 0405901 | 1/1991 | European Pat. Off. . |
| 0405902 | 1/1991 | European Pat. Off. . |
| 0415296 | 3/1991 | European Pat. Off. . |
| 0496361 | 7/1992 | European Pat. Off. . |
| 0510673 | 10/1992 | European Pat. Off. . |
| 2140064 | 12/1973 | France . |
| 8806624 | 9/1988 | WIPO . |
| 9100279 | 3/1991 | WIPO . |

OTHER PUBLICATIONS

Patent Abstracts of Japan, vol. 13, No. 278, C611, Abstract of JP 01–74986, Publ. 1989–03–20 (KAO Corp.).

*Primary Examiner*—David M. Naff
*Assistant Examiner*—Jon P. Weber
*Attorney, Agent, or Firm*—Steve T. Zelson, Esq.; Elias J. Lambiris, Esq.

[57] ABSTRACT

An alkaline serine protease is disclosed which is obtainable from Bacillus sp. JA16-38A, NCIMB No. 40263 and which (a) has a pH optimum in the range of 9–11 determined at 25° C.; (b) has a temperature optimum in the range of 40°–50° C. determined at pH 9.5; (c) is active in the presence of ethylene-diamine tetraacetate; and (d) has a mass of about 28 kD determined by SDS-PAGE. Detergent additives and detergent compositions comprising said protease and methods for producing said protease are also disclosed.

13 Claims, 1 Drawing Sheet

ALKALINE PROTEASES OBTAINABLE FROM BACILLUS SP. JA16-38A

TECHNICAL FIELD

This invention is in the field of detergent proteases derived from strains of alkalophilic Bacillus sp. More specifically, the invention is directed towards a novel alkaline protease derived from a strain of Bacillus sp. JA16-38A. Moreover, the invention is directed towards a process for the preparation of the protease, the use of the protease as detergent enzyme, and detergent compositions comprising the protease of the invention.

BACKGROUND ART

Detergent enzymes have been marketed for more than 20 years and are now well established as normal detergent ingredients in both powder and liquid detergents all over the world. With the trend towards lower temperature washing, detergent enzyme consumption has increased during late years. Enzymes used in washing formulations comprise proteases, lipases, amylases, cellulases, as well as other enzymes, or mixtures hereof. Commercially most important are proteases.

Detergent proteases have been developed by isolation of proteases found in nature followed by testing in detergent formulations. Most detergent proteases are obtained from members of the genus Bacillus. Currently new types of proteases enter the market, offering the possibility of giving a better cost/performance ratio at various specified conditions.

Examples of commercial protease products are ALCALASE™, ESPERASE™ and SAVINASE™, all supplied by Novo Nordisk NS, Denmark. These and similar enzyme products from other commercial sources are active in detergent solutions, i.e. at pH values in the range of from 8 to 11 and in the presence of sequestering agents, surfactants and bleaching agents such as sodium perborate. The ALCALASE™ protease is produced by strains of the species Bacillus licheniformis. The ESPERASE™ and SAVINASE™ proteases are obtained by cultivation of strains of alkalophilic Bacilli.

It is an object within the present invention to provide novel detergent proteases with improved cost/performance ratio.

SUMMARY OF THE INVENTION

According to the present invention there are provided novel detergent proteases.

In its first aspect, the invention provides a protease having an apparent molecular weight of 28 kD, a pI around 6.4, pH optimum in the range of from pH 9 to 11 (at 25° C.), temperature optimum in the range of from 40° to 50° C. (at pH 9.5), and immunochemical properties identical or partially identical to those of a protease derived from Bacillus sp. JA16-38A, NCIMB No. 40263, in a more specific aspect, the protease is obtainable from a strain of Bacillus sp. JA16-38A. In a yet more specific aspect, the protease is obtainable from Bacillus sp. JA16-38A, NCIMB No. 40263, or a mutant or a variant thereof.

In another aspect, the invention provides an isolated biologically pure culture of a strain of Bacillus sp. JA16-38A. In a more specific aspect, a strain of Bacillus sp. JA16-38A, NCIMB No. 40263, or a mutant or a variant thereof, is provided.

In a third aspect, the invention provides a process for the preparation of the protease, which process comprises cultivation of a protease producing strain of Bacillus sp. JA16-38A in a suitable nutrient medium, containing carbon and nitrogen sources and inorganic salts, followed by recovery of the desired enzyme. In a more specific aspect, Bacillus sp. JA16-38A, NCIMB No. 40263, or a mutant or a variant thereof, is cultivated.

In a fourth aspect, the use of the enzyme as detergent enzyme is claimed. In a more specific aspect, the invention provides a detergent composition and a detergent additive comprising the protease.

BRIEF DESCRIPTION OF DRAWINGS

The present invention is further illustrated by reference to the accompanying drawings, in which.

DETAILED DISCLOSURE OF THE INVENTION

The microorganism

Figure 1:
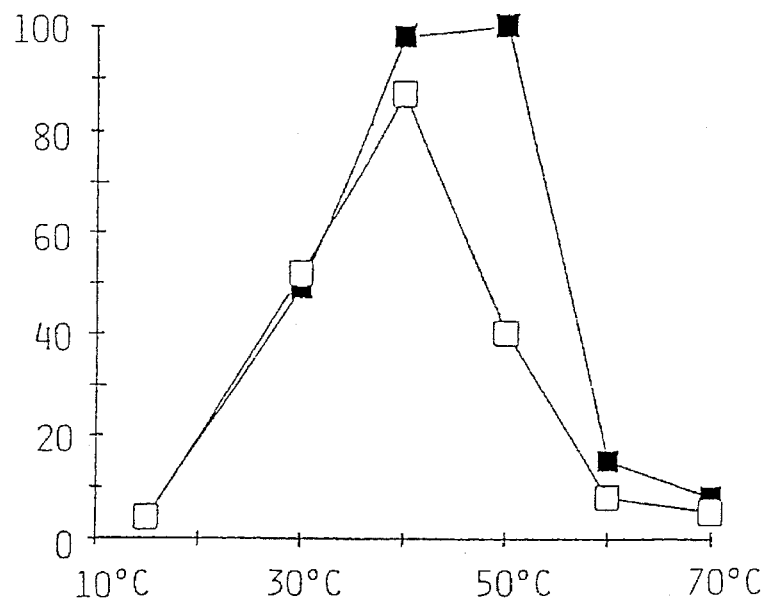
FIG. 1 shows the relation between temperature and the proteolytic activity of an enzyme according to the invention (the enzyme preparation obtained according to Ex. 1, with casein as substrate and at pH 9.5)

The novel microorganisms of the invention, able to produce an enzyme of the invention, were isolated essentially by the method for selection of alkalophilic Bacilli described in British Patent No. 1,243,784. One such culture, Bacillus sp. JA16-38A, has been deposited according to the Budapest Treaty at NCIMB, under No. 40263.

The microorganism of this invention is an aerobic, spore forming bacterium belonging to the genus Bacillus. Morphologically it can be described as motile rods with a diameter of 0.6–0.8 micron, and a length of 2–3 micron. The spores are round to ellipsoid, not swelling the sporangium, central to subterminal. Optimal temperature for growth is within 35°–40° C., and optimal pH for growth is within 8.5–9.5, no growth below pH 8, and no growth at 50° C. The microorganism forms white to colourless transparent colonies on nutrient agar slants, and no diffusion of pigment into the agar is observed.

The microorganism of the invention can be further characterized by the test results cited in Table 1.

TABLE 1

| TEST | DSM 485 | DSM 497[2] | JA16-38A |
|---|---|---|---|
| Nutrient agar (Difco) pH 9[1] | + | + | + |
| Nutrient agar (Difco) pH 7[1] | w | − | w |
| Nutrient agar (Difco) pH 11[1] | + | − | − |
| B. Subtilis minimal medium (Spizizen) pH 7[1] | w | − | w |
| Growth at 50° C.[1] | − | + | − |
| Growth in NaCl: | | | |
| 2% | − | + | − |
| 5% | − | + | − |
| 7% | − | + | − |
| 10% | − | + | − |
| Hydrolysis of: | | | |
| Starch | + | + | + |
| Casein | + | + | + |
| Gelatin | + | + | + |
| CMC | − | − | − |

TABLE 1-continued

| TEST | DSM 485 | DSM 497[2] | JA16-38A |
|---|---|---|---|
| Acid from: | | | |
| Glucose | + | W | + |
| Mannitol | – | + | – |
| Sorbitol | – | | – |
| Xylose | – | | – |
| Reduction of: | | | |
| Nitrate | – | – | + |
| Anaerobic growth | – | – | – |
| Voges Proskauer reaction | – | – | – |

DSM 485: B. alkalophilus
DSM 497: B. alkalophilus subsp. halodurans
JA16-38A: B. sp. JA16-38A, NCIMB No. 40263
W = Weak
[1]Recorded after incubation for 2 days. All other incubations for 7 days.
[2]Data from literature
[3]Positive after incubation for 14 days, negative after 7 days.

Cultivation of the microorganism

The microorganism of the invention can be cultivated under aerobic conditions in a nutrient medium containing assimilable carbon and nitrogen together with other essential nutrients, the medium being composed in accordance with the principles of the known art.

Suitable carbon sources are carbohydrates such as sucrose, glucose and starch, or carbohydrate containing materials such as soy bean grits, cotton seed flour, cereal grain, malt, rice and sorghum. The carbohydrate concentration incorporated in the medium may vary widely, e.g. up to 25% and down to 1–5%, but usually 8–10% will be suitable, the percentages being calculated as equivalents of glucose.

The nitrogen source in the nutrient medium may be of inorganic and/or organic nature. Suitable inorganic nitrogen sources are nitrates and ammonium salts. Among the organic nitrogen sources quite a number are used regularly in fermentation processes. Illustrative examples are soybean meal, cotton seed meal, peanut meal, casein, corn, corn steep liquor, yeast extract, urea and albumin. In addition, the nutrient medium should also contain usual trace substances.

Since the novel Bacillus species of this invention are alkalophilic, and growing weakly at pH below 8, the cultivation is preferably conducted at alkaline pH values, which can be obtained by addition of suitable buffers such as sodium carbonate or mixtures of sodium carbonate and sodium bicarbonate, after sterilization of the growth medium. For cultivation in tank fermentors it is necessary to use artificial aeration. The rate of aeration is similar to that used in conventional tank fermentation.

Recovery and purification of the proteases

After fermentation, the extracellular proteases produced by the microorganisms can be recovered and purified according to principles of the known art, e.g. using steps like removal of coarse materials from the culture broth by centrifugation or drum filtration, concentration of the broth by evaporation or ultrafiltration, and purification by anion-exchange chromatography or precipitation with acetone, followed by affinity chromatography. Finally, preservatives may be added to the purified proteases.

Assay for proteolytic activity

The proteolytic activity is determined with casein as substrate. One Casein Protease Unit (CPU) is defined as the amount of enzyme liberating 1 mM of primary amino groups (determined by comparison with a serine standard) per minute under standard conditions, i.e. incubation for 30 minutes at 25° C. and pH 9.5. A folder AF 228/1, describing the analytical method, is available upon request to Novo Nordisk NS, Denmark, which folder is hereby included by reference.

The enzyme

The enzyme of the invention is a novel detergent protease. It is an alkaline protease, obtainable by cultivation of a microorganism of the invention, preferably Bacillus sp. JA16-38A, NCIMB No. 40263, or a mutant or a variant thereof, in a suitable nutrient medium, containing carbon and nitrogen sources and inorganic salts. The enzyme can also be obtained by recombinant DNA-technology.

The protease of the invention can be described by the following characteristics.

Physical-chemical properties

A molecular weight of 28 kD, determined by SDS-PAGE. A pI of 6.4 determined by isoelectric focusing on LKB Ampholine® PAG plates. The protease activity is inhibited by PMSF, α-1-antitrypsine and Turkey-egg-white proteinase inhibitor. EDTA and soybean-protein inhibitor do not influence the protease activity.

The temperature-activity relationship was determined with casein as substrate. The assay for proteolytic activity described previously was used with the modification that the incubation temperature was varied in the interval of from 15° to 70° C. The result is shown in FIG. 1. The enzyme possesses proteolytic activity from temperatures below 15° C. to above 70° C., and a temperature optimum within the range of 40° to 50° C., around 45° C.

Figure 2:
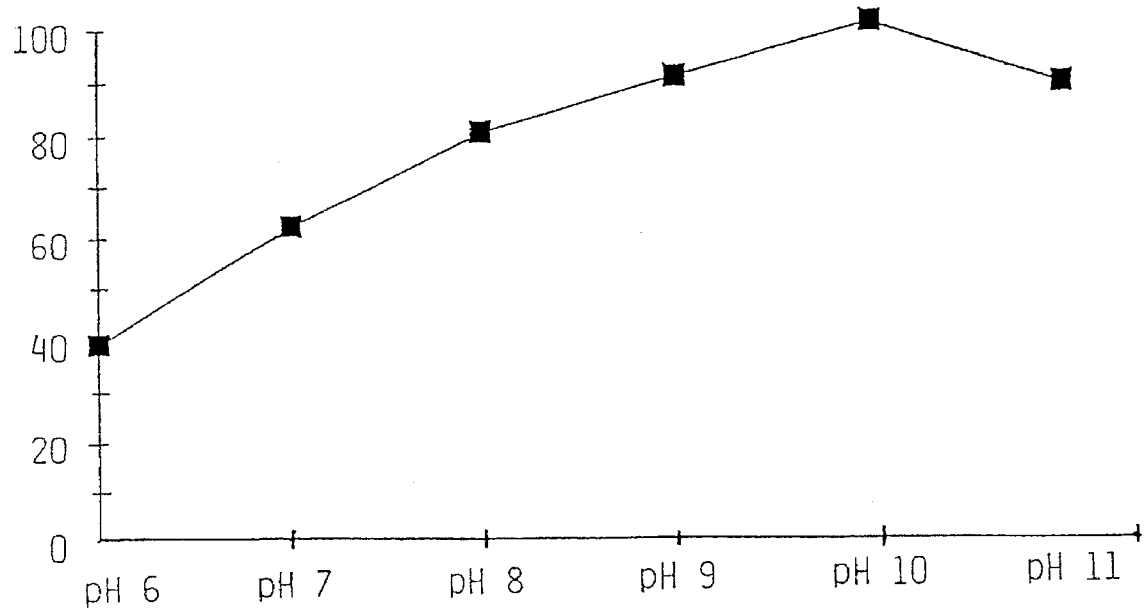
FIG. 2 shows the relation between pH and the proteolytic activity of an enzyme according to the invention (the enzyme preparation obtained according to Ex. 1, with casein as substrate and at 25° C.).

The dependence of activity on pH was determined by the same procedure, using buffers adjusted to predetermined pH values in the pH range of from 6 to 11. The result is shown in FIG. 2. The enzyme possesses proteolytic activity at pH values below 6 to above 11, with a pH optimum in the range pH 9 to pH 11, around pH 10.

The protease of the invention has an extremely high specific activity against casein, corresponding to above 300 CPU per gram of enzyme protein, as determined by active site titration (vide e.g. Schonbaum, G. R., Zerner, B. & Bender, M. L. (1961); J. Biol. Chem.; 236 2930).

The protease of the invention is stable for 60 minutes at 40° C. and under washing conditions, both with and without bleaches such as perborate and NOBS, in European and American type detergents.

Immunochemical properties

The immunochemical properties can be determinated immunologically by cross-reaction identity tests. The identity tests can be performed by the well-known Ouchterlony double immunodiffusion procedure or by tandem crossed immunoelectrophoresis according to Axelsen, N. H.; Handbook of Immunoprecipitation-in-Gel Techniques; Blackwell Scientific Publications (1983), chapters 5 and 14. The terms "antigenic identity" and "partial antigenic identity" are described in the same book, chapters 5, 19 and 20.

Monospecific antiserum was generated according to the above mentioned method by immunizing rabbits with the purified protease of the invention. The immunogen was mixed with Freund's adjuvant and injected subcutaneously into rabbits every second week. Antiserum was obtained after a total immunization period of 8 weeks, and immunoglobulin was prepared therefrom as described by N. H. Axelsen, supra.

Ouchteriony double immunodiffusion tests showed no cross reaction between the protease of the invention and the known alkaline serine proteases ALCALASE™, SAVINASE™, ESPERASE™, subtilisin BPN' and KAZUSASE™.

Detergent compositions

The detergent composition of the invention may comprise one or more surfactants, which may be of an anionic, non-ionic, cat-ionic, amphoteric or zwitterionic type, or a mixture of these. Typical examples of artionic surfactants are linear alkyl benzene sulfonates (LAS), alkyl sulfates (AS), alpha clefin sulfonates (AOS), alcohol ethoxy sulfates (AES) and alkali metal salts of natural fatty acids. Examples of non-ionic surfactants are alkyl polyethylene glycol ethers, nonylphenol polyethylene glycol ethers, fatty acids, esters of sucrose and glucose, and esters of polyethoxylated alkyl glucoside.

The detergent composition of the invention may also contain other detergent ingredients known in the art such as builders, bleaching agents, bleach activators, anti-corrosion agents, sequestering agents, anti soil-redeposition agents, perfumes, stabilizers for the enzymes and bleaching agents, formulations aids, optical brighteners, foam boosters, chelating agents, fillers, fabric softeners, etc. The detergent composition of the invention may be formulated substantially as described in J. Falbe [Falbe, J.; Surfactants in Consumer Products. Theory, Technology and Application; Springer Verlag 1987, vide in particular the section entitled "Frame formulations for liquid/powder heavy-duty detergents"].

It is at present contemplated that the detergent composition of the invention may contain the enzyme preparation in an amount corresponding to 0.0005–0.5 CPU of the proteolytic enzyme per liter of washing liquor.

The detergent compositions of the invention can be formulated in any convenient form, such as powders, liquids, etc.

The detergent composition of the invention may advantageously include one or more other enzymes, e.g. lipases, amylases, cellulases, oxidases and/or peroxidases, conventionally included in detergent compositions.

The protease of the invention may be included in a detergent composition by adding separate additives containing the detergent protease, or by adding a combined additive comprising different detergent enzymes.

The additive of the invention can be formulated e.g. as granulates, liquids, slurries, etc. Preferred detergent additive formulations are non-dusting granulates, liquids, in particular stabilized liquids, slurries, or protected enzymes. Dust free granulates may be produced e.g. according to GB Patent Publication No. 1,362,365 or U.S. Pat. No. 4,106,991, and may optionally be coated by methods known in the art. The detergent enzymes may be mixed before or after granulation. Liquid enzyme preparations may, for instance, be stabilized by adding a polyol such as e.g. propylene glycol, a sugar or sugar alcohol, lactic acid or boric acid, according to established methods. Other enzyme stabilizers are well known in the art. Protected enzymes may be prepared according to the method disclosed in EP Patent Publication No. 238,216.

In useful embodiments the protease of the invention may be incorporated in detergent formulations according to e.g. EP Patent Publication Nos. 342,177; 368,575; 378,261; and 378,262.

The invention is further illustrated in the following examples, which are not intended to be in any way limiting to the scope of the invention as claimed.

EXAMPLE 1

Preparation Example

Bacillus sp. JA16-38A was cultivated at 25° C. on a rotary shaking table (300 r.p.m.) in 500 ml baffled Edenmeyer flasks containing 100 ml of medium of the following composition (per liter):

| Potato starch | 100 g |
| Ground barley | 50 g |
| Soybean flour | 20 g |
| $Na_2HPO_4 \times 12\ H_2O$ | 9 g |
| Pluronic® | 0.1 g |
| Sodium caseinate | 10 g |

The starch in the medium is liquified with α-amylase and the medium is sterilized by heating at 120° C. for 45 minutes.

After sterilization the pH of the medium is adjusted to 9.7 by addition of 10 ml of a 1M solution of sodium sesquicarbonate.

After 5 days of incubation the proteolytic activity of the culture was determined using the method described above.

After cultivation, the enzyme activity of the broth was 100 CPU/l.

After separation of the solid material the protease was purificated by a conventional chromatographic method.

Yield from 1 l of culture broth was 5.0 ml with 1500 CPU/l. Purity was more than 90% as judged by SDS-PAGE.

The characteristics of the preparation prepared in accordance with this Example have been referred to earlier in this specification, and reference is made hereto.

EXAMPLE 2

Wash performance

The wash performance tests were accomplished on grass juice soiled cotton, in a model wash system at 20° C., isothermically for 10 minutes.

2.0 g/l of an American type powder detergent composition were used in the test. The detergent did not contain any enzymes prior to the addition of the protease of the invention. The detergent was dissolved in approx. 6° dH (German Hardness) water. The textile/wash liquor ratio was approximately 6 g textile per liter of detergent solution. The pH was 9.5. Two independent tests were performed. The enzyme preparation according to Example 1 was used in a dosage as cited in Table 1.

Subsequent to washing, the fabric was rinsed in running tap water for 25 minutes and air-dried. The protease performance was determined by the change (ΔR) of the remission (%R) at 460 nm measured on a Datacolor Elrephometer 2000, ΔR being the remission after wash with protease added minus the remission after wash with no protease added.

The result of the test is shown in Table 1.

TABLE 1

| concentration; | delta R |
| --- | --- |
| 0.0025 CPU/l | 1.46 |
| 0.005 CPU/l | 1.88 |
| 0.01 CPU/l | 2.62 |
| 0.02 CPU/l | 6.15 |
| 0.04 CPU/l | 9.83 |
| 0.08 CPU/l | 11.22 |
| 0.2 CPU/l | 12.20 |

The differential remission values show that the protease of the invention possesses good wash performance.

EXAMPLE 3

Stability in detergents

The stability of an enzyme of the invention (obtained according to Ex. 1) in the presence of detergents was tested.

The detergents used in this test were the American type powder detergent composition also used in Example 2.

The residual activity was measured after 60 minutes at 40° C. in 1.1 g detergent/l and 6 °dH water of JA16-38A protease (0.3 CPU/l). The residual activity measured was 90%.

This experiment shows that the protease is stable in detergents under washing conditions.

We claim:

1. An isolated protease obtainable from Bacillus sp. JA16-38A, NCIMB No. 40263 which:
   (a) has a pH optimum in the range of 9–11 determined at 25° C.;
   (b) has a temperature optimum in the range of 40°–50° C. determined at pH 9.5;
   (c) is active in the presence of ethylene-diamine tetraacetate; and
   (d) has immunochemical properties identical to those of a protease obtained from Bacillus sp. JA16-3gA, NCIMB No. 40263.

2. An isolated protease according to claim 1 which has an apparent molecular weight of about 28 kD determined by SDS-PAGE.

3. An isolated protease according to claim 1 which has an isoelectric point of about 6.4.

4. The protease according to claim 1 which is obtained from Bacillus sp. JA16-38A, NCIMB No. 40263 or a mutant thereof which produces said protease.

5. The protease according to claim 1 which has a specific activity against casein of 300 CPU per gram of enzyme protein determined by active site titration.

6. The protease according to claim 1 which is inhibited by phenylmethylsulphonylfluoride, α-1-antitrypsin and Turkey-egg-white proteinase inhibitor.

7. The protease according to claim 1 which is active in the presence of soybean-protein inhibitor.

8. The protease according to claim 1 which has a residual activity of 90% after 60 minutes at 40° C. determined at washing conditions in the presence and in the absence of perborate or nonanoyloxybenzenesulfonate.

9. A process for producing the protease according to claim 1, comprising:
   (a) cultivating in a suitable nutrient medium a strain of Bacillus, wherein the nutrient medium comprises carbon and nitrogen sources and inorganic salts; and
   (b) recovering said protease.

10. The process according to claim 9, wherein the strain is Bacillus sp. JA16-38A, NCIMB No. 40263 or a mutant thereof which produces said protease.

11. A detergent additive, comprising the isolated protease according to claim 1, wherein said detergent additive is in the form selected from the group consisting of a non-dusting granulate, a liquid, a slurry and a protected enzyme.

12. A detergent composition comprising the isolated protease according to claim 1 and a surfactant.

13. The detergent composition according to claim 12, further comprising one or more other enzymes selected from the group consisting of amylases, lipases, cellulases, oxidases and peroxidases.

* * * * *